(12) United States Patent
Netravali et al.

(10) Patent No.: US 9,839,531 B2
(45) Date of Patent: Dec. 12, 2017

(54) PROCESS FOR CREATING BONE CAVITIES FOR BONE HEALING

(71) Applicant: Think Surgical, Inc., Fremont, CA (US)

(72) Inventors: Nathan A Netravali, Palo Alto, CA (US); In K Mun, Nanuet, NY (US)

(73) Assignee: Think Surgical, Inc, Fremont, CA (US)

( * ) Notice: Subject to any disclaimer, the term of this patent is extended or adjusted under 35 U.S.C. 154(b) by 0 days.

(21) Appl. No.: 14/777,405

(22) PCT Filed: Mar. 17, 2014

(86) PCT No.: PCT/US2014/030126
§ 371 (c)(1),
(2) Date: Sep. 15, 2015

(87) PCT Pub. No.: WO2014/145373
PCT Pub. Date: Sep. 18, 2014

(65) Prior Publication Data
US 2016/0038244 A1    Feb. 11, 2016

Related U.S. Application Data

(60) Provisional application No. 61/787,994, filed on Mar. 15, 2013.

(51) Int. Cl.
*A61F 2/36* (2006.01)
*A61F 2/46* (2006.01)
(Continued)

(52) U.S. Cl.
CPC ............ *A61F 2/4607* (2013.01); *A61B 17/17* (2013.01); *A61B 19/2203* (2013.01);
(Continued)

(58) Field of Classification Search
CPC ...................................................... A61F 2/3607
See application file for complete search history.

(56) References Cited

U.S. PATENT DOCUMENTS 5,086,401 A * 2/1992 Glassman .............. A61B 34/20
606/53
8,152,783 B2    4/2012 Swain
(Continued)

FOREIGN PATENT DOCUMENTS

WO       2014045119 A2    3/2014

OTHER PUBLICATIONS

Cohan, S. "ROBODOC achieves pinless registration" The Industrial Robot; 2001; 28, 5; ProQuest p. 381.
(Continued)

*Primary Examiner* — Thomas J Sweet
*Assistant Examiner* — Megan Wolf
(74) *Attorney, Agent, or Firm* — Avery N. Goldstein; Blue Filament Law PLLC

(57) ABSTRACT

A process and system for performing orthopedic surgery to create a series of channels with a subject's bone to allow a reduced pressure system to be applied directly to the bone-implant interface to enhance bone healing is provided. The process for to promote healing of a bone of a subject includes creating a three-dimensional model of the bone; preoperatively planning a location of an implant relative to the model; creating a plan for the location of precision channels that reach the bone-implant interface based on the model and the implant; resurfacing the bone to fit the implant into or onto the bone based on the preoperative plan; and milling the precision channels into the bone in the location to promote healing of the bone and/or bone implant interface; and applying a pressure reduction system at the bone-implant interface to promote bone healing.

20 Claims, 3 Drawing Sheets

(51) Int. Cl.
*A61B 17/17* (2006.01)
*A61B 19/00* (2006.01)
*A61B 34/32* (2016.01)
*A61F 2/28* (2006.01)
*A61B 17/56* (2006.01)
*A61B 34/10* (2016.01)
*A61B 90/00* (2016.01)

(52) U.S. Cl.
CPC .............. *A61B 19/50* (2013.01); *A61B 34/32* (2016.02); *A61F 2/36* (2013.01); *A61F 2/4644* (2013.01); *A61B 2017/564* (2013.01); *A61B 2019/5466* (2013.01); *A61B 2019/5483* (2013.01); *A61B 2034/102* (2016.02); *A61B 2034/105* (2016.02); *A61B 2034/107* (2016.02); *A61B 2090/3975* (2016.02); *A61B 2217/005* (2013.01); *A61F 2002/286* (2013.01); *A61F 2002/4615* (2013.01); *A61F 2002/4645* (2013.01); *A61F 2002/4685* (2013.01)

(56) References Cited

U.S. PATENT DOCUMENTS

| | | |
|---|---|---|
| 8,267,918 B2 | 9/2012 | Johnson et al. |
| 2005/0080423 A1* | 4/2005 | Hagan ................ A61B 17/8822 606/86 R |
| 2006/0212158 A1 | 9/2006 | Miller |
| 2007/0218101 A1* | 9/2007 | Johnson ................ A61B 17/88 424/423 |
| 2009/0270868 A1 | 10/2009 | Park et al. |
| 2011/0245929 A1 | 10/2011 | Rakin et al. |
| 2011/0251483 A1* | 10/2011 | Razzaque ............. A61B 6/466 600/424 |
| 2015/0025548 A1* | 1/2015 | Franklin ............. G06F 17/5009 606/130 |

OTHER PUBLICATIONS

Besl, Paul J. and McKay, Neil D. "A Method for Registration of 3-D Shapes", Member, IEEE Transactions on Pattern Analysis and Machine Intelligence, Feb. 1992; 14, No. 2, pp. 239-256.

* cited by examiner

PROCESS FOR CREATING BONE CAVITIES FOR BONE HEALING

CROSS-REFERENCE TO RELATED APPLICATION

This application claims priority of U.S. Provisional Patent Application Ser. No. 61/787,994 filed Mar. 15, 2013, which is incorporated herein by reference.

FIELD OF THE INVENTION

The present invention relates generally to the field of orthopedic surgery for the healing of bone tissue, and more specifically to a new and useful system and process for creating specific three-dimensional (3D) shapes in specific locations in bone to aid in the creation of a reduced pressure system to enhance bone healing after joint replacement or bone injury.

BACKGROUND OF THE INVENTION

Bone is a living tissue that is constantly changing through the resorption of matrix tissue by osteoclasts and the deposition of new matrix tissue by osteoblasts. Joint replacement arthroplasty is an orthopedic procedure in which the surface of the joint is replaced with a prosthetic component, or implant. It typically requires the removal of the articulating cartilage surface of the joint including a varying amount of bone depending on the joint and the replacement implant such that the bone surface matches the backside of the implant. This cartilage and bone is then replaced with a synthetic, typically metal implant that is used to create a new joint surface. Repair of a bone fracture or replacement of a portion of a bone after injury or when removing a tumor often requires the insertion or attachment of a separate member that spans the fracture. For example, a bone fracture may be repaired using a metal plate that spans the break and is attached to the bone using screws.

In the case of joint replacement, the stability and longevity of the implant is dependent on how well it is fixed to the bone. Many implants rely on bone ingrowth into the implant to achieve this stable fixation. Recently, processes have been proposed to use a reduced pressure treatment to bone to achieve osteogenic activity for fracture repair or bone healing (see for example U.S. Pat. No. 8,267,918 B2 and U.S. Pat. No. 8,152,783 B2). However, in the case of a joint replacement, it is difficult to achieve this level of pressure reduction at the bone-implant interface.

Thus, there exists a need for a more efficient process to create a reduced pressure environment directly at the bone-implant interface.

SUMMARY OF THE INVENTION

A process and system for performing orthopedic surgery to create a series of channels within a bone of a subject to allow a reduced pressure system to be applied directly to the bone-implant interface to enhance bone healing. The process to promote healing of a bone of a subject includes creating a three-dimensional model of the bone; resurfacing the bone to fit an implant into the bone or onto a surface of the bone based on the model; milling precision channels into the bone in a location that reaches a bone-implant interface; inserting the implant into the bone in contact with the bone-implant interface; and applying a pressure reduction system at the bone-implant interface to promote the healing of the bone of the subject. Preoperative planning is used to predict a location of an implant relative to the bone model. A plan is developed for the location of precision channels that reach the bone-implant interface based on the model and the implant.

The inventive process may be used for the replacement of hip joints, shoulder joints, ankle joints, wrist joints, finger joints, toe joints, or other joints. The inventive orthopaedic surgery can be performed on human; or an animal of a non-human primate, a horse, a cow, a sheep, a goat, a dog, a cat, a rodent, and a bird.

DESCRIPTION OF THE INVENTION

The present invention has utility as a system and process for performing orthopaedic surgery. The following description of various embodiments of the invention is not intended to limit the invention to these specific embodiments, but rather to enable any person skilled in the art to make and use this invention through exemplary aspects thereof. Disclosed herein is a process to create a series of channels with a bone of a subject to allow a reduced pressure system to be applied directly to the bone-implant interface to enhance bone healing. Reference will be made herein to the replacement of hip joints and it should be understood that the present invention may be applied to other joints within the body and any other bones found within the body. These other joints that are repaired through resort to the present invention illustratively include the hip joint, shoulder joint, ankle joint, wrist joint, finger joint, toe joint, or other joint. As used herein, a subject is defined as a human; or an animal of a non-human primate, a horse, a cow, a sheep, a goat, a dog, a cat, a rodent, and a bird.

Figure 1:
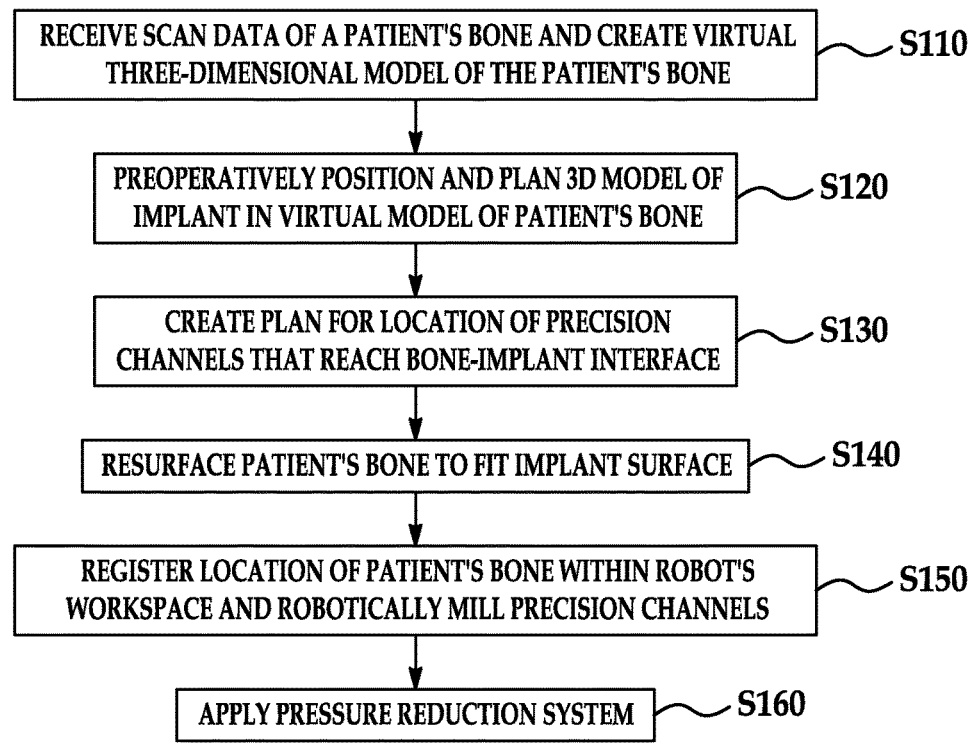
FIG. 1 is a flowchart depicting a specific embodiment of the present invention for using a robotic milling system to create a series of precision channels in the subject bone during joint arthroplasty to allow a reduction in pressure.

With reference to FIG. 1, an embodiment of an inventive process is detailed for creating a three-dimensional model of a subject's bone and may include the steps of receiving scan data of a subject's bone and creating a virtual three-dimensional model of the subject's bone in block S110; preoperatively planning the location of a 3D virtual model of the implant relative to the virtual model of the subject's bone in block S120; creating a plan for the location of precision channels that reach the bone-implant interface based on the virtual models of the subject's bone and implant in block S130; resurfacing the subject's bone to fit the implant into or onto the bone based on the preoperative plan in block S140; registering the location of the actual bone during the surgery such that the precise position and orientation of the bone is known by the robot and then robotically milling the precision channels into the bone in the location predetermined in the virtual model in block S150; and finally applying the pressure reduction system at the bone-implant interface to promote bone healing.

Scan data of the bone of a subject for creating a virtual three-dimensional model of the subject's bone and cartilage of block S110 is readily provided from conventional sources subject such as computer tomography (CT), magnetic resonance imaging (MRI), or X-ray scans of subjects' bones, or a combination thereof. Modelling software such as VSG Amira or Medviso Segment is readily used to convert imaging scans into a model of bone of interest. The scan data may be collected by a system and process described herein or may alternatively, be collected prior to the creation of a series of precision channels by a system and process specific to the bone imaging technique.

The preoperative positioning and planning a virtual three-dimensional model of an implant or multiple implants relative to the virtual model of the subject's bone is provided at block S120. In certain embodiments of the present invention a model of the subject's bone is created using surgical preoperative planning software. Additionally, block S120 in still other embodiments also functions to create instructions for a robotic system to mill out the implant shape into the bone to create a cavity that accurately matches the backside of the implant that will be placed into or onto the bone. One such robotic system is the ROBODOC System, manufactured by Curexo Technology Corporation of Fremont, Calif.

The creation of a plan for the location(s) of precision channels from the surface of the bone to the bone-implant interface is provided at block S130. In some embodiments, there may be only one channel, while in others, multiple channels may be required. It is appreciated that the precision channels may be of any shape or volume but must provide a channel from the bone-implant interface to the surface of the bone. In certain inventive embodiments, the implant will have a specific region on its surface that may be coated with a material or have a special surface topography designed to enhance bone ingrowth; while in still other embodiments, the precision channels will create a channel that reaches this specific region. In some embodiments, the implant may have the specific region designed to contact the bone and other regions not designed to contact the bone. In these cases, the precision channels are positioned to reach these regions. The precision channels may be of any size ranging from microscopic channels to having a diameter of several centimeters. Bone ingrowth enhancing substances illustratively include osteoblasts, osteocytes, donor bone cells, stem cells or other pluripotential cells, hydroxyapatite coated metals, and proteinaceous substances such as TGF-$\alpha$,-$\beta$1, -2; EGF, IGF-I; PDGF, FGF, BMP-1, VEGF, or a combination thereof.

The resurfacing of the subject's bone to fit the implant surface is provided at S140. In a certain inventive embodiment, this resurfacing will be done using a robotic system which will create a precise surface that matches the shape of the implant. In another embodiment, this resurfacing is done using a manual technique such as a broach and reamer for a total hip arthroplasty implant or a mechanical jig, drill, and oscillating saw for a total knee arthroplasty implants. In certain inventive embodiments, the location of the implant cavity is exactly known as it had been planned during the preoperative planning described in block S120 thereby rendering the resurfacing amenable to robotic resurfacing as detailed hereafter.

The registration of the location of the bone intraoperatively within the workspace of the robot is provided at block S150. This serves to determine the precise location and orientation of the bone within the workspace of the robot. In some embodiments, this may be accomplished using fiducial markers placed into or on the bone. A fiducial marker is appreciated to be a material with an opacity that is different than that of surround subject tissue such that it can be identified in an image and used as a point of reference or measure, an active device such as a radio frequency identification (RFID) tag, or a combination thereof. In still other embodiments, this may use a registration guide is applied that fits on the bone. In some embodiments, this may use a surface matching algorithm or any other process to determine the orientation of the subject bone. The usage of such techniques are further detailed in: PCT/IB2013/002311 entitled SYSTEM AND METHOD FOR REGISTRATION IN ORTHOPAEDIC APPLICATIONS. S. Cohan, "ROBODOC achieves pinless registration" The Industrial Robot; 2001; 28, 5; pg. 381. P. J. Besl, "A Method for Registration of 3-D Shapes" IEEE Transactions on Pattern Analysis and Machine intelligence, 1992; 14, pgs. 239-256.

In certain inventive embodiments, this registration will take place prior to resurfacing the subject's bone to fit the implant surface described in block S140. However, it is appreciated that this registration may take after the subject's bone has been resurfaced, especially in cases where the resurfacing is performed using a manual technique instead of being performed by a robotic system. Once the location and orientation of the bone is known in the workspace of the robot, the robot automatically uses a mill, drill, or other cutting mechanism based on instructions created in the preoperative planning software to create the precision channels in the exact locations chosen in the preoperative planning described in block S130. The shape, location, size, and number of precision channels created in the bone by the robotic system will preferably match planned precision channels described in block S130. There may be a reason to reduce or skip the number of precision channels compared to the preoperative plan during the surgery, so there shall be an option to skip certain robotic actions creating the channels.

A pressure reduction system is applied to the bone-implant interface to enhance bone-implant ingrowth and healing at block S160. In certain inventive embodiments, a seal or flexible barrier is placed along the outside surface of the subject bone encompassing the precision channels created in block S150. A vacuum or reduced pressure system is then attached to the sealed portion to reduce the pressure within the precision channel or channels to the bone-implant interface. In some embodiments, a precision channel is filled with a scaffolding material or flowable material to fill the void. In these embodiments, it is important that the filling material contains a plurality of flow channels such that reduced pressure applied at the outer surface of the bone will result in reduced pressure at the bone-implant interface. The filling material in certain inventive embodiments is made of a bio-absorbable substance that does not need to be removed from the subject's body. Bio-absorbable substances operative herein illustratively include Poly(glycolic acid) (PGA), Poly(lactic acid) (PLA), and copolymers thereof. In other embodiments, hydroxyapatite-coated metals, ceramics, bone chips, or nanocrystalline domains represent non-biodegradable substances that are readily retained within the bone and overgrown through bone ingrowth.

Figure 2:
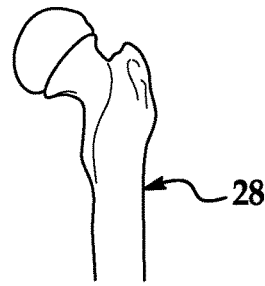
FIG. 2 is a schematic block diagram of an inventive system for creating a three-dimensional model of a subject's bone based on scanned input data and a plan for placing a series of precision channels in the subject bone along with instructions for a robotic machine to mill out the precision channels.
Figure 2:
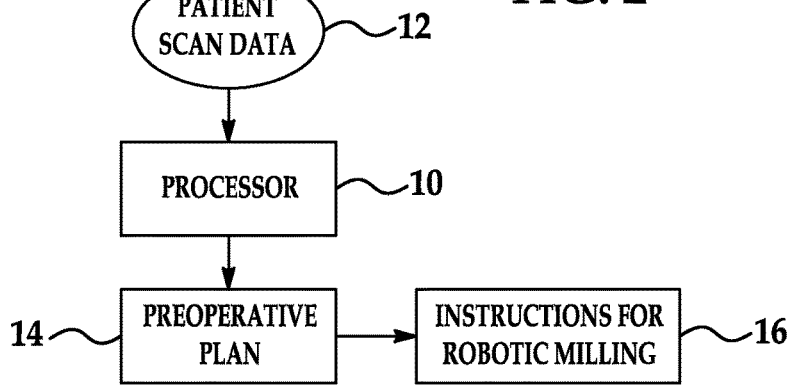
Figure 4:
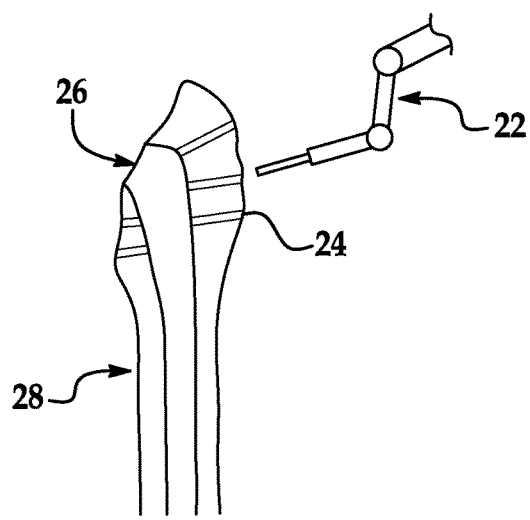
FIG. 4 illustrates a robotic milling tool creating the precision channels within the bone after the implant cavity has already been created.

As shown in FIG. 2, a system for creating a three-dimensional model of a subject's bone 28 includes a processor 10 configured to receive subject scan data 12 and to transform the subject scan data into a three-dimensional virtual model. The system then allows the user to create a preoperative plan 14 that includes locations and dimensions for precision channels that reach the bone-implant interface, which the system then translates into instructions for a robotic milling system to create the precision channels in the exact locations created in the preoperative plan. In some embodiments, the processor 10 may automatically create the planned precision channel locations and sizes based on the implant chosen in the preoperative planning software to ensure that the channels are place in regions that require bone-implant ingrowth. The processor 10 in certain embodiments allows the user to modify the customized shape as they choose. The inventive system in certain embodiments functions to automatically create a three-dimensional model of a subject's bone based on the subject scan data input. The system in certain embodiments functions to create a three-dimensional model of a subject's bone in sufficient detail that the subject's real bone can be registered accurately to the three-dimensional model. The processor 10 in certain embodiments creates instructions for a robotic milling tip 22, as shown in FIG. 4, to precisely mill out the cavity in the bone. The system is readily used for joint replacement bone healing and bone-implant ingrowth in orthopedic surgery, but may alternatively be used for any suitable applications, clinical or otherwise.

As shown in FIG. 2, the processor 10 is configured to receive subject scan data 12 and to transform the subject scan data into instructions 16 for a robotic system to mill out precision channels in the subject's bone during surgery. The processor 10 in certain embodiments functions to create instructions for the creation of a three dimensional surface model based on the subject scan data. In still other embodiments, the processor may run preoperative surgical planning software. In some embodiments, the scan data may be in the form of CT, MRI, or X-ray scans of subjects' bones. The scan data may be collected by the systems and processes described herein or may alternatively, is collected prior to the creation of the custom milled bone shape by systems and processes specific to imaging.

Figure 3:
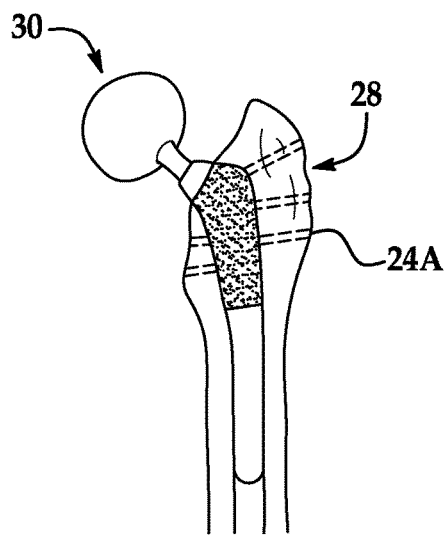
FIG. 3 illustrates a preoperative plan of a virtual model of a subject's bone with a virtual model of an implant placed within the bone along with the planned locations for precision channels.

As shown in FIG. 3, a virtual model of the subject's bone is created with an implant 30 positioned within the subject's bone 28. In certain embodiments, the planned locations and sizes of precision channels (shown in ghost) 24A are selected and visualized using preoperative planning software. The user then has the option to modify the shape, size, number, and location of the precision channels 24 using preoperative planning software. It is appreciated that a physical model of the bone 28 is readily formed with a conventional three dimensional printer or transferring the virtual model data to a computer-aided design (CAD) operated milling machine to aid in channel planning.

As shown in FIG. 4, an implant cavity 26 is created in the bone 28 by resurfacing the bone. In certain embodiments, this resurfacing will be done using a robotic system which will create a precise surface 26 that matches the shape of the implant. In another embodiment, this resurfacing will be done using a manual technique such as a broach and reamer for a total hip arthroplasty implant or a mechanical jig, drill, and oscillating saw for a total knee arthroplasty implants. In still other embodiments, the location of the implant cavity will be exactly as it had been planned during the preoperative planning described in block S120 of FIG. 1.

As further shown in FIG. 4, where like numeral have the meaning associated with the aforementioned drawings, once the location and orientation of the bone is known in the workspace of the robot, the robot automatically uses a mill, drill, or other cutting mechanism based on instructions created in the preoperative planning software to create the precision channels in the exact locations chosen in the preoperative planning. The shape, location, size, and number of precision channels 24 created in the bone by the robotic system 22 will preferably match planned precision channels 24A. There may be a reason to reduce or skip the number of precision channels compared to the preoperative plan during the surgery, so in certain embodiments an option is provided to skip certain robotic actions creating the channels 24. The movement of the robotic system 22 in certain embodiments will be automatic and predetermined based on the preoperative planning.

Figure 5:
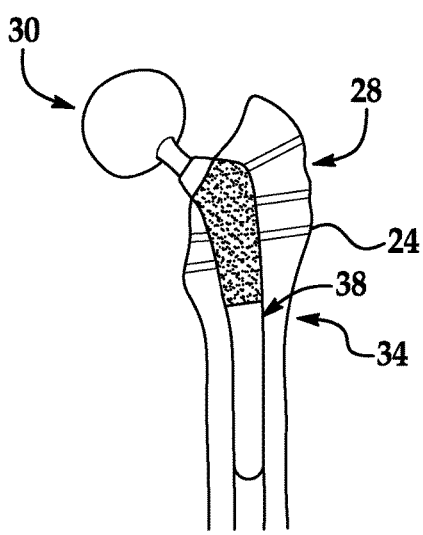
FIG. 5 illustrates the subject bone after the implant has been placed within the bone and the precision channels have been created.

As shown in FIG. 5, where like numeral have the meaning associated with the aforementioned drawings, once the implant cavity 26 and precision channels 24 have been created, the implant 30 is placed onto the surface of the bone 28 or into the bone 28. The implant cavity 26 in certain embodiments is the same size, or slightly smaller than the implant 30 such that when the implant 30 is placed within the cavity 26, there is direct contact between the bone 28 and the implant 30 creating a bone-implant interface 38; while in other embodiments a gap is provided to accommodate a bonding agent, mesh, pharmaceutical, or other interfacial material so desired.

Figure 6:
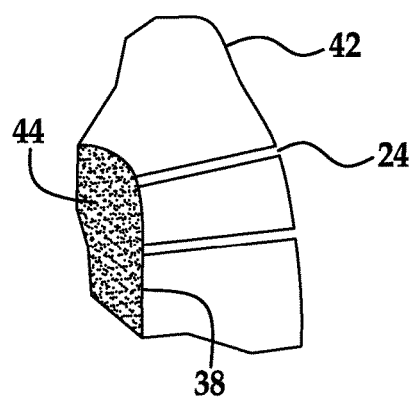
FIG. 6 illustrates the subject bone after the implant has been placed within the bone and a pressure reduction system has been applied to reduce the pressure at the bone-implant interface.

As shown in FIG. 6, a close-up cross-sectional view of the interface between the bone 28 and the implant 30 where like numeral have the meaning associated with the aforementioned drawings, the precision channels 26 are created such that they create a direct channel from the outer surface 42 of the bone 28 to the bone-implant interface 38 and contacting the surface of the implant 44. In some embodiments, the precision channels 24 are created after the implant 30 has been placed into the bone and it is still necessary for the precision channels to begin from the outer surface of the bone and end at the bone-implant interface 38.

Figure 7:
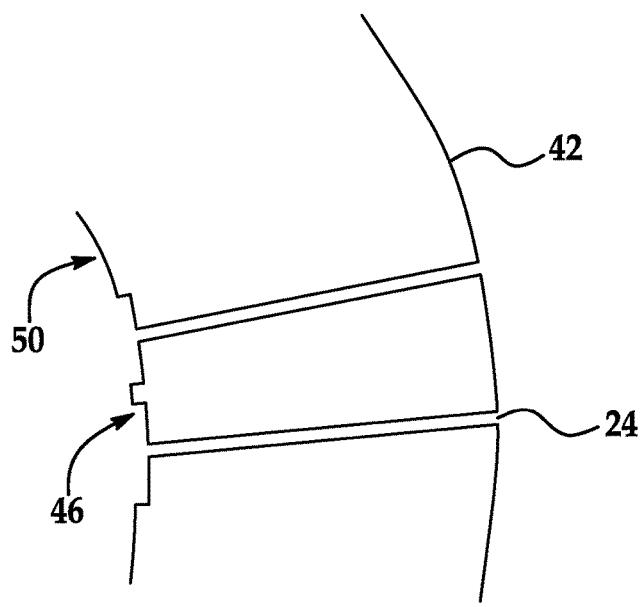

As shown in FIG. 7, a close-up cross sectional view of the inside surface 50 of the bone cavity 28 is provided where like numeral have the meaning associated with the aforementioned drawings, there may be a need to add a specific pattern 46 on the inside surface 50 of the bone 28. This pattern 46 may or may not be connected to the precision channels 24. The user will have the ability to control the size, depth, and length of this pattern based on a clinical need using the preoperative planning station and the robotic system will produce this pattern on the bone surface that will mate with the implant.

Figure 8:
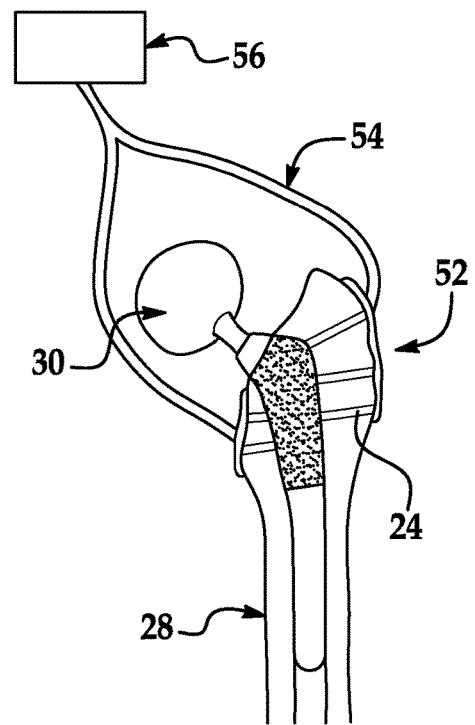

As shown in FIG. 8, once the implant 30 has been placed into the bone 28 and the precision channels have been created within the bone, a flexible barrier or seal 52 in some inventive embodiments is applied to the outer surface of the bone completely enclosing the precision channels 24 that have been created. A reduced pressure creation tube 54 is connected on one end to the flexible barrier 52 and on the other end to an apparatus that can reduce the pressure within the tube, such as a vacuum or a pump. The flexible barrier 52 and pressure creation tube 54 are readily formed of a bio-absorbable material, such as Poly(glycolic acid) (PGA), Poly(lactic acid) (PLA), and copolymers thereof, that may not need to be removed from the subject's body. The pressure reduction apparatus 56 will reduce the pressure in the pressure creation tube 54, thereby reducing the pressure at the bone-implant interface, as the bone grows into the implant and heals. As the bone-implant interface heals, the pressure creation tube 54 and flexible barrier 52 may be removed from the subject. The precision channels 26 are readily used to inject medications, bone growth promoting proteins, bone growth promoting cells, or other treatments illustratively including healing or growth factors such as TGF-α,-β1, -2; EGF, PDGF, FGF, BMP-1, VEGF, or a combination thereof through some of the precision channels, while maintaining a vacuum through other bone cavities or precision channels such that the drugs are cycled through the bone-implant interface. The medications may be introduced through one or more injection tubes (not shown) that are integrated into the flexible barrier 52, where separate injection tubes may be used to segregate the drugs being introduced to the implant area.

References recited herein are indicative of a level of skill in the art to which the invention pertains. These references are hereby incorporated by reference to the same extent as if each individual reference was explicitly and individually incorporated herein by reference.

As a person skilled in the art will recognize from the previous detailed description and from the figures and claims, modifications and changes can be made to the preferred embodiments of the invention without departing from the scope of this invention defined in the following claims.

We claim:

1. A process to promote healing a bone of a subject comprising:
   creating a three-dimensional model of a bone;
   resurfacing the bone to fit an implant into the bone based on the model;
   robotically milling precision cylindrical channels into the bone extending from a surface of the bone to a bone-implant interface;
   inserting the implant into the bone in contact with the bone-implant interface and the precision cylindrical channels; and
   applying a pressure reduction system at the bone-implant interface to promote the healing of the bone of the subject.

2. The process of claim 1 further comprising receiving scan data of the bone.

3. The process of claim 2 wherein the scan data is provided from at least one source of CT scans of the bone of the subject, MRI scans of the bone of the subject, X-ray scans of the bone of the subject, or a combination thereof.

4. The process of claim 2 wherein said three-dimensional model is created from said scan data with modelling software.

5. The process of claim 1 wherein creating the three-dimensional model of the bone is a virtual three-dimensional model of the bone created with surgical preoperative planning software.

6. The process of claim 1 further comprising registering the location of the bone during a surgery such that a precise position and an orientation of the bone is known to a robot and then robotically performing the milling.

7. The process of claim 6 wherein a set of fiducial markers placed into or on the bone assist in determining the precise position and orientation of the bone within a workspace of the robot.

8. The process of claim 7 wherein said set of fiducial markers are formed of a material with an opacity that is different than that of the surrounding bone tissue such that said set of fiducial markers can be identified in an image.

9. The process of claim 7 wherein said set of fiducial markers are an active device comprising a radio frequency identification (RFID) tag.

10. The process of claim 6 wherein registering the location of the bone further comprises applying a registration guide on the bone or a surface matching algorithm.

11. The process of claim 1 wherein the bone is part of a hip joint.

12. The process of claim 1 wherein the bone is part of a knee joint, a shoulder joint, an ankle joint, a wrist joint, a finger joint, or a toe joint.

13. The process of claim 1 wherein the pressure reduction system further comprises a flexible barrier or seal applied to the outer surface of the bone that completely encloses the precision cylindrical channels, and a reduced pressure creation tube that is connected on a proximal end to the flexible barrier and on a distal end to a vacuum or pump that can reduce the pressure within the tube and by extension reduce the pressure at the bone-implant interface.

14. The process of claim 13 wherein the flexible barrier and the pressure creation tube are made of a bio-absorbable material, and further comprising retaining the flexible barrier with the subject.

15. The process of claim 14 wherein the bio-absorbable material comprises Poly(glycolic acid) (PGA), or Poly(lactic acid) (PLA), or copolymers thereof.

16. The process of claim 13 further comprising removing the pressure creation tube and flexible barrier from the subject as the bone-implant interface heals.

17. The process of claim 13 further comprising injecting at least one of medications, bone growth promoting proteins, or bone growth promoting cells through a first set of the precision cylindrical channels, while maintaining a vacuum through a second set of the precision cylindrical such that the medications, bone growth promoting proteins, or bone growth promoting cells are cycled through the bone-implant interface.

18. The process of claim 17 wherein the at least one of medications, bone growth promoting proteins, or bone growth promoting cells are introduced through one or more injection tubes that are integrated into the flexible barrier, where separate injection tubes are used to segregate the medications being introduced.

19. The process of claim 1 wherein the bone is resurfaced to fit an implant into the bone using conventional manual tools.

20. The process of claim 1 wherein the bone is resurfaced to fit an implant into the bone using a robotic system by registering the location of the bone during a surgery such that a precise position and an orientation of the bone is known to a robot and then robotically resurfacing the bone.

* * * * *